(12) United States Patent
Koveshnikov (10) Patent No.: US 6,896,727 B2
(45) Date of Patent: May 24, 2005

(54) METHOD OF DETERMINING NITROGEN CONCENTRATION WITHIN A WAFER

(75) Inventor: Sergei V. Koveshnikov, Vancouver, WA (US)

(73) Assignee: SEH America, Inc., Vancouver, WA (US)

( * ) Notice: Subject to any disclaimer, the term of this patent is extended or adjusted under 35 U.S.C. 154(b) by 320 days.

(21) Appl. No.: 10/184,666

(22) Filed: Jun. 28, 2002

(65) Prior Publication Data

US 2004/0000267 A1 Jan. 1, 2004

(51) Int. Cl.$^7$ ............................................... C30B 29/06
(52) U.S. Cl. ..................... 117/2; 117/3; 117/13; 117/15; 117/932
(58) Field of Search ........................... 117/2, 3, 13, 15, 117/932

(56) References Cited

U.S. PATENT DOCUMENTS

| 6,059,875 A | 5/2000 | Kirkland et al. |
| 6,224,668 B1 | 5/2001 | Tamatsuka |

OTHER PUBLICATIONS

Tobe et al, "Equilibrium constant of segragation–induced Fe gettered by heavy boron doping in Si", Journal of Applied Physics vol. 84 no3. pp. 1279–1283 abstract only, Aug. 1998.*
Yang et al., "Nitrogen in Czochralski Silicon" IEEE 2001 6th conference on Solid–State and Integrated Circuit pp. 255–260 2001.*

* cited by examiner

Primary Examiner—Robert Kunemund
(74) Attorney, Agent, or Firm—Alston & Bird LLP (57) ABSTRACT

An improved method of determining the concentration of nitrogen within a wafer is provided. At least a portion of the nitrogen within the wafer is initially gettered to a gettering site. In order prevent the in-diffusion of nitrogen, a barrier layer is generally deposited upon the wafer prior to gettering the nitrogen within the wafer. The nitrogen is then measured at the gettering site. The concentration of nitrogen within the wafer is then determined based upon the measurement of nitrogen at the gettering site and the diffusion coefficient for nitrogen. In this regard, the diffusion coefficient of nitrogen permits the measurement of nitrogen at the gettering site to be translated into a measurement of the concentration of nitrogen throughout the entire wafer.

20 Claims, 5 Drawing Sheets

METHOD OF DETERMINING NITROGEN CONCENTRATION WITHIN A WAFER

FIELD OF THE INVENTION

The present invention relates generally to a method of determining the nitrogen concentration within a wafer and, more particularly, to a method for accurately determining the nitrogen concentration within a wafer based upon a diffusion coefficient for nitrogen.

BACKGROUND OF THE INVENTION

Semiconductor wafers or substrates, such as silicon wafers, may include nitrogen. The nitrogen may be introduced into the wafer either intentionally or unintentionally. For example, the wafer may intentionally be doped with nitrogen, such as by introducing nitrogen into the molten material from which an ingot is drawn and from which wafers are subsequently cut. Nitrogen may also diffuse into a wafer at various stages of the fabrication process. For example, the wafer may be annealed or otherwise processed at an elevated temperature in an environment that includes nitrogen, thereby causing nitrogen to diffuse into the wafer.

Regardless of the manner in which a wafer is doped with nitrogen, it is oftentimes advantageous to determine the concentration of nitrogen within the wafer since the presence and, more particularly, the concentration of nitrogen within the wafer affects at least some of the properties of the wafer. For example, the presence of nitrogen serves to encourage the precipitation of oxygen in the bulk portion of a wafer. In this regard, the nitrogen serves as nucleation sites for oxygen, thereby accelerating oxygen precipitation in the bulk portion of a wafer. By encouraging the precipitation of oxygen within a wafer, the resistivity of the wafer can be tailored and may have a relatively high resistance as described by co-pending U.S. patent application Ser. No. 10/008,404, filed Dec. 6, 2001, entitled High Resistivity Silicon Wafer Having Electrically Inactive Dopant And A Method Of Producing Same, the contents of which are incorporated in their entirety herein.

Conventionally, the nitrogen concentration of a wafer has not been directly measured from the wafer. Instead, an estimate of the nitrogen concentration of the wafer would generally be established based upon the concentration of nitrogen available as a dopant during the fabrication of the wafer. For example, the eventual concentration of nitrogen within the wafer may be estimated based upon the concentration of the nitrogen provided as a dopant in the molten material from which an ingot is drawn and from which the wafer is thereafter sliced. Alternatively, the concentration of nitrogen within a wafer may be estimated based upon the concentration of nitrogen in the surrounding environment while the wafer is being annealed or is otherwise subjected to elevated temperatures.

As will be apparent, estimates of the nitrogen concentration within a wafer based upon the nitrogen concentration that was provided as a dopant during the process of fabricating the wafer may not be entirely accurate. With the increased specificity with which wafers and their properties are being defined by the microelectronic industry, it would be desirable to determine the concentration of nitrogen within a wafer with greater specificity. As such, it would be desirable to develop a method for more accurately and directly measuring the concentration of nitrogen within a wafer.

BRIEF SUMMARY OF THE INVENTION

An improved method of determining the concentration of nitrogen within a wafer is therefore provided. By directly determining the concentration of nitrogen within the wafer, the method of the present invention may be capable of determining the concentration of nitrogen in a more accurate fashion than conventional techniques that estimate the nitrogen concentration within the wafer based upon the concentration of nitrogen available as a dopant during the process of fabricating the wafer.

According to the present invention, at least a portion of the nitrogen within the wafer is gettered to a gettering site. The gettering site may be formed as a gettering layer within the wafer, such as by implanting ions within the wafer to define the gettering layer. Once the gettering site has been formed within the wafer, a barrier layer is typically deposited on the wafer prior to gettering at least a portion of the nitrogen within the wafer to the gettering site. In this regard, the barrier layer, such as an oxide layer, prevents the in-diffusion of nitrogen from the surrounding environment. Thus, while the nitrogen is thereafter gettered to the gettering site, such as by heating the wafer, nitrogen will be unable to in-diffuse from the surrounding environment to the gettering site.

Once at least a portion of the nitrogen within the wafer has been gettered, the nitrogen is measured at the gettering site. More typically, the nitrogen is measured throughout a portion of the wafer that includes the gettering site. By depositing a barrier layer on the wafer prior to gettering the nitrogen, the nitrogen that is measured at the gettering site is generally limited to nitrogen within the wafer since the in-diffusion of nitrogen from the surrounding environment is effectively prevented by the barrier layer.

The concentration of nitrogen within the wafer is then determined based upon the measurement of nitrogen at the gettering site and the diffusion coefficient for nitrogen. In this regard, the diffusion coefficient of nitrogen permits the measurement of nitrogen at the gettering site to be translated into a measurement of the concentration of nitrogen throughout the entire wafer. In this regard, the diffusion coefficient for nitrogen, in combination with the length of time for which the wafer was heated during the gettering process may be utilized to determine the diffusion length. As such, the nitrogen measured throughout the portion of the wafer that includes the gettering site may be divided by the diffusion length of the nitrogen in order to determine the concentration of the nitrogen within the wafer.

By directly measuring the nitrogen within the wafer and thereafter determining the concentration of the nitrogen within the wafer based upon this direct measurement, the method of the present invention therefore emits an accurate determination of the concentration of nitrogen within the wafer.

According to another aspect of the present invention, a method is provided for determining the diffusion coefficient for nitrogen. According to this method, first and second wafers are provided. Each wafer has a gettering site and includes an epitaxial layer. The epitaxial layer of each wafer has a different thickness. Nitrogen is then permitted to in-diffuse from the surrounding environment to the gettering site of each wafer, such as by heating the wafer in an environment that includes nitrogen. The nitrogen is then measured at the gettering site of each wafer and the diffusion coefficient for nitrogen is determined based at least partially upon the nitrogen measured at the gettering site of each wafer. As such, the method of this aspect of the present invention permits the diffusion coefficient for nitrogen to be readily determined. The value of the diffusion coefficient of the nitrogen may then be utilized to determine the concentration of nitrogen within a wafer according to the advantageous method of the present invention described above.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
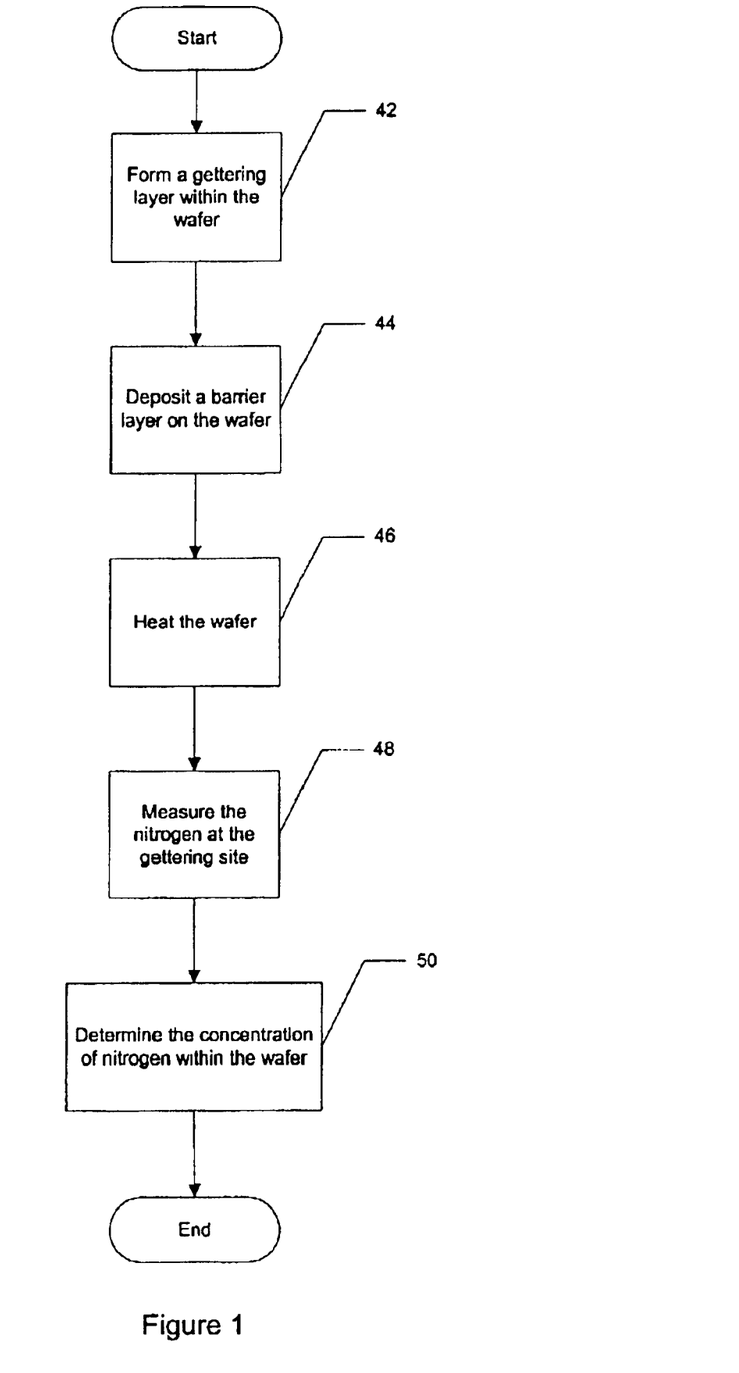
FIG. 1 is a flow chart illustrating the operations performed to measure the nitrogen concentration within a wafer according to a method of one embodiment of the present invention.

As shown in FIG. 1, a method is therefore provided according to the present invention for determining the concentration of nitrogen within a wafer. Typically, the method of the present invention will be utilized to determine the concentration of nitrogen within a silicon wafer. As such, examples of the various steps of the method are provided in the context of the determination of the concentration of nitrogen within a silicon wafer. However, the method of the present invention may be utilized to determine the concentration of nitrogen within other types of wafers, if so desired. As described below, the concentration of nitrogen within the wafer is directly measured according to the method of the present invention and, as such, may be more accurate than the conventional estimate of the concentration of nitrogen within a wafer based upon the concentration of nitrogen available as a dopant during the process of fabricating the wafer.

Figure 2:
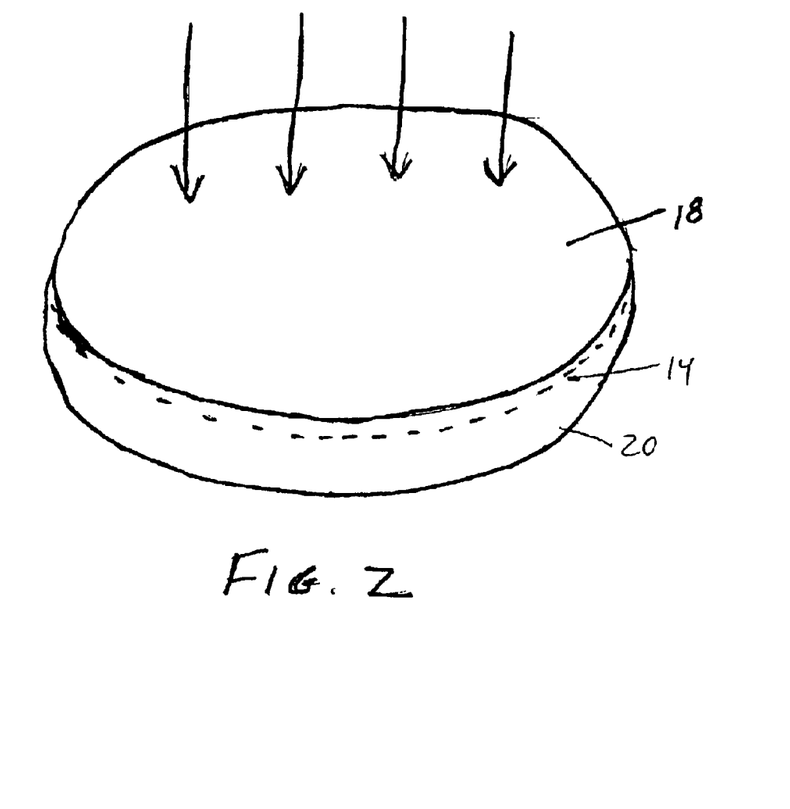
FIG. 2 is a perspective view of a wafer depicting the ion implantation of a gettering layer therewithin.

The method initially getters at least a portion of the nitrogen within the wafer to a gettering site. In order to determine the concentration of nitrogen within the wafer, the wafer is preferably protected from the in-diffusion of nitrogen from the surrounding environment. As such, the nitrogen gettered to the gettering site will be the nitrogen present in the bulk of the wafer, as opposed to nitrogen that has diffused into the wafer. In order to getter at least a portion of the nitrogen within the wafer to a gettering site, a wafer is initially provided that includes a gettering site. In this regard, a gettering site and, more commonly, a gettering layer may be initially formed within the wafer as indicated by block 42 of FIG. 1. While a gettering layer may be formed in various manners as known to those skilled in the art, the gettering layer 14 may be formed by ion implantation as illustrated generally in FIG. 2. In ion implementation, ions are implanted at a predefined depth relative to a surface 18 of the wafer 20. The depth at which the ions are implanted and at which the gettering layer is therefore defined can vary, but is typically between 0 and 5 microns from the surface of the wafer. In one embodiment, for example, the ions are implanted to depth of between 0.01 microns and 0.1 microns from the surface of the wafer. Various ions may be implanted, but in embodiments in which the wafer is formed of silicon, the implanted ions may be Si+ ions.

Figure 3:
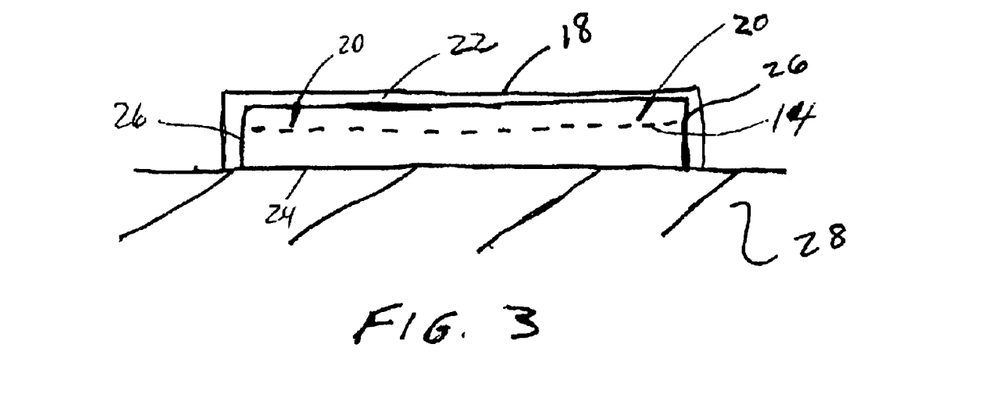
FIG. 3 is a cross-sectional view of the wafer having a gettering layer and coated with a barrier layer to prevent the in-diffusion of nitrogen.

In order to prevent the in-diffusion of nitrogen from the surrounding environment, a barrier layer 22 may be deposited on the wafer 20 after the gettering site 14 has been defined, but prior to actually gettering nitrogen to the gettering site. See block 44 of FIG. 1. The barrier layer is typically formed on all surfaces of the wafer that will be exposed to the surrounding environment during the gettering process. In this regard, both major surfaces of the wafer, such as the front and back surfaces 18 and 24, as well as the side surface 26 of the wafer may be coated with a barrier layer. Alternatively, in embodiments as shown in FIG. 3 in which the wafer rests upon a support surface 28 such that the one major surface is not exposed to the surrounding environment, the other major surface, such as the front surface, and the side surface of the wafer are coated with the barrier layer.

The barrier layer 22 is formed of a material and has a thickness that are selected to effectively prevent the in-diffusion of nitrogen during the gettering process. Typically, the barrier layer may be an oxide, such as a silicon dioxide layer deposited upon a silicon wafer, and may have a thickness of about 0.3 microns. As will be apparent to those skilled in the art, the barrier layer may be formed of other materials and may have other thicknesses depending upon the composition of the wafer and the conditions to which the wafer will be subjected during the gettering process. For example, a wafer that will be subjected to a gettering process that operates at a higher temperature and/or for a more extended period of time will generally require a barrier layer that is somewhat more impervious, such as a thicker barrier layer, than the barrier layer of a wafer that will be subjected to a gettering process that is of a shorter duration and/or at a lower temperature.

In order to getter the nitrogen within the wafer 20 to the gettering site 14, the wafer is typically heated as depicted by block 46 of FIG. 1. The wafer is generally heated at a predefined temperature for a predetermined length of time in order to getter at least a portion of the nitrogen from within the wafer to the gettering site. The predefined temperature and the predetermined length of time are selected such that a sufficient quantity of the nitrogen, such as a substantial majority of the nitrogen within the wafer proximate the gettering site, may be gettered to the gettering site. In one embodiment, for example, a silicon wafer having a gettering layer formed of Si+ ions at a depth of between 0.01 microns and 0.1 microns from the surface of the wafer is annealed at a temperature between 900° C. and 1100° C. for one hour. In order to further reduce the likelihood of in-diffusion of nitrogen or other contaminants from the surrounding environment, the wafer not only includes a barrier layer 22, but is also typically annealed in an atmosphere of pure $O_2$.

Upon completion of the gettering process, the wafer 20 is analyzed to measure the nitrogen at the gettering site 14. See block 48 of FIG. 1. More typically, the nitrogen is measured throughout a portion of the wafer that includes the gettering site, such as the nitrogen located between a surface 18 of the wafer and some predefined depth within the wafer that is greater than the depth at which the gettering site 14 is located. For example, in an embodiment in which the wafer includes a gettering layer about 4 microns below the surface of the wafer, the nitrogen may be measured from the surface of the wafer to a depth of about 6, 8 or 10 microns from the surface of the wafer. As such, the portion of the wafer that is analyzed includes the gettering site as well as at least some portion of the wafer on either side of the gettering site, i.e., some portion of the wafer closer to the surface of the wafer than the gettering site and some portion of the wafer further removed from the surface of the wafer than the gettering site. The nitrogen at or around the gettering site may be measured in various manners including by means of secondary ion mass spectrometry (SIMS), as known to those skilled in the art.

Figure 4:
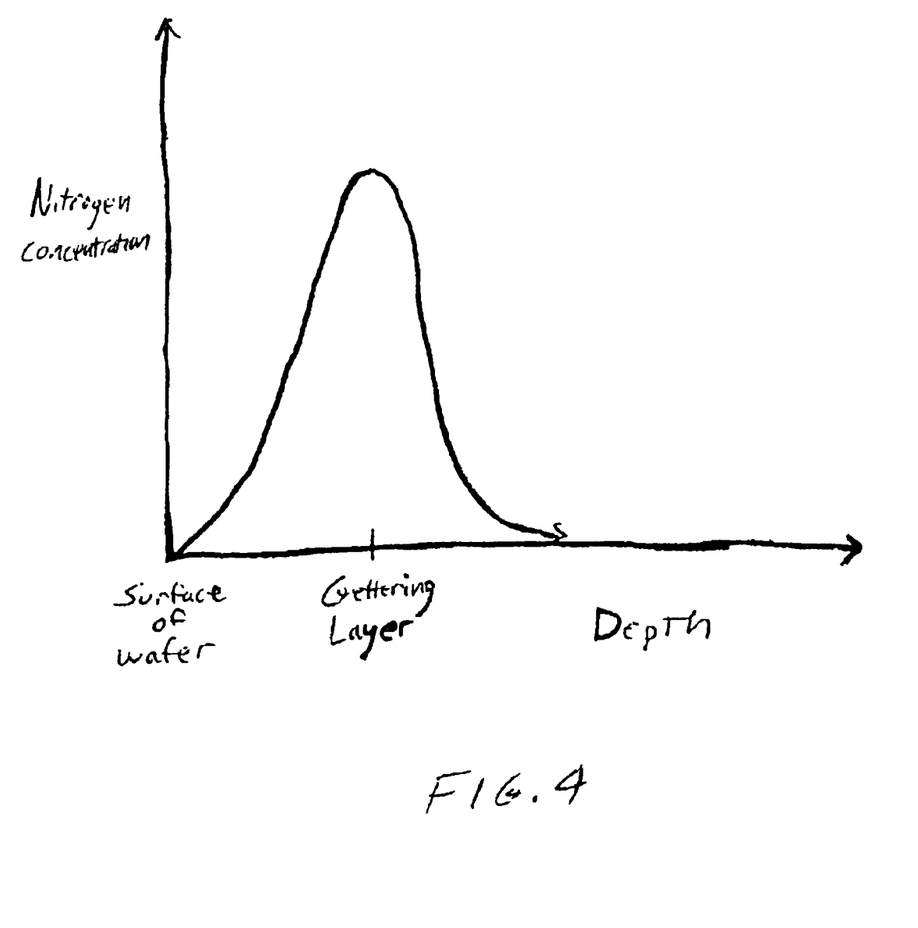
FIG. 4 is a graph representing the nitrogen measured within a portion of the wafer that includes a gettering layer.

As a result of the attraction of the nitrogen to the gettering site 14 upon activation of the wafer 20, such as by heating the wafer, the nitrogen that is measured within the wafer is generally much greater at the gettering site than at other portions of the wafer. As shown in FIG. 4, for example, the concentration of nitrogen measured from the surface of a wafer to some depth within the wafer that is greater than the depth at which the gettering site is located defines a curve, such as a gaussian curve, that is relatively sharply peaked at the depth within the wafer corresponding to the location of the gettering site, thereby indicating a relatively large concentration of nitrogen.

As known to those skilled in the art, the gettering of nitrogen to the gettering site 14 does not collect all of the nitrogen within the wafer 20. As such, the nitrogen that is measured at and around the gettering site must then be further processed in order to determine the concentration of nitrogen within the wafer. See block 50 of FIG. 1. As explained below, this further processing must take into account the diffusion length L of nitrogen and, in turn, the diffusion coefficient D of nitrogen. In order to determine the concentration of nitrogen within the wafer based upon the measurement of nitrogen at and around the gettering site, the nitrogen that is measured at and around the gettering site is summed, such as by integrating the area under the curve, such as the curve shown in FIG. 4, representing the nitrogen measured at various depths within the wafer on both sides of the gettering site. Based upon this integration, a measure of the nitrogen at and around the gettering site is determined on a per square centimeter basis, i.e., in units of $cm^{-2}$. By dividing the results of the integration of the area under the curve representing the nitrogen measured at and around the gettering site by the diffusion length L of nitrogen, the concentration of nitrogen within the entire wafer may be determined since the diffusion length L of nitrogen takes into account the distance through the wafer that the nitrogen may diffuse during the predetermined period of time τ that the wafer is activated, such as by heating. In this regard, the diffusion length L of nitrogen is defined as follows:

$$L = \sqrt{D\tau}$$

wherein D is the diffusion coefficient for nitrogen and τ is the length of time during which the wafer is activated, such as by heating.

For a given temperature utilized during the heating of the wafer 20 to getter the nitrogen at the gettering site 14, the diffusion coefficient D of nitrogen is a constant. The value of the diffusion coefficient of nitrogen for wafers heated at a predetermined temperature may be known to those skilled in the art, e.g., see T. Ito and T. Abe, *Applied Physics Letters*, Vol. 53, 39 (1988), which is hereby incorporated by reference, or may be determined in various manners, one of which is described below. According to the article by T. Ito and T. Abe, those skilled in the art can obtain the diffusion coefficient D of nitrogen for wafers heated at a predetermined temperature using the following equation.

$$D = 2.7 \times 10^3 \exp\left(\frac{-2.8 \text{ eV}}{kT}\right) \frac{cm^2}{\sec}$$

where k is the Boltzman's constant and T is the temperature.

Regardless of the manner in which the diffusion coefficient D of nitrogen is determined, the concentration of nitrogen within the wafer may be determined based upon the measurement of nitrogen at and around the gettering site and the diffusion coefficient D of nitrogen. In particular, the concentration of nitrogen within the wafer may be determined by dividing the result of the integration of the area under curve representing the nitrogen measured at and around the gettering site by the diffusion length L of nitrogen, as described above.

The method of the present invention therefore permits the concentration of nitrogen within the wafer 20 to be determined based upon a direct measurement of the nitrogen within the wafer and, more particularly, the nitrogen in and around the gettering site 14. The determination of the concentration of nitrogen within the wafer provided according to the method of the present invention may be more accurate than the conventional estimates of the concentration of nitrogen within the wafer based upon the concentration of nitrogen available as a dopant during the process of fabricating the wafer.

As noted above, the diffusion coefficient D for nitrogen may be provided in various manners. According to one aspect of the present invention depicted in FIG. 5, however, a method for determining the diffusion coefficient D for nitrogen is provided. In this regard, at least two and, in some instances, more wafers are provided, with each wafer having a gettering site 14, such as a gettering layer. See block 60. These wafers are generally the same type of wafers that will be thereafter analyzed to determine the nitrogen concentration as described above. As such, the wafers may be silicon wafers having a gettering layer defined by the ion implantation, of Si+ ions. Each of these wafers also includes an epitaxial layer, such as a silicon epitaxial layer formed upon a silicon wafer. However, the epitaxial layer of each wafer preferably has a different thickness. For example, a first wafer may have an epitaxial layer with a thickness of about 4 microns and a second wafer may have an epitaxial thickness of about 16 microns.

Figure 5:
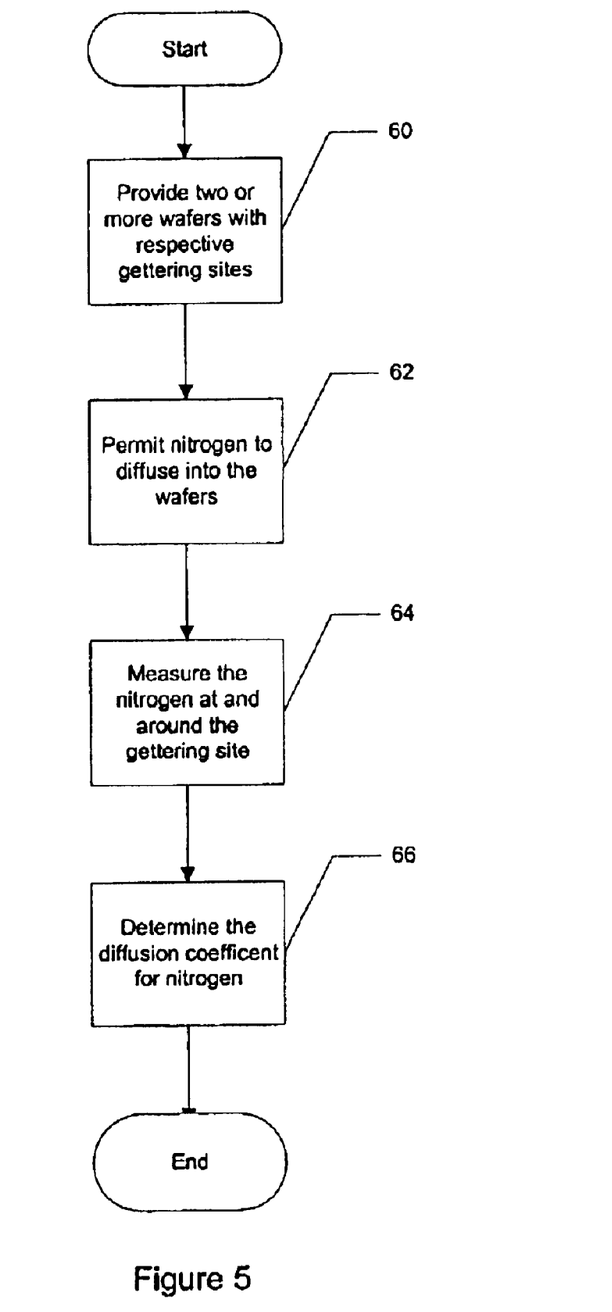
FIG. 5 is a flow chart illustrating the operations performed to determine the diffusion coefficient of nitrogen according to one aspect of the present invention.

Each wafer 20 is then processed in a manner that permits the in-diffusion of nitrogen from the surrounding environment. See block 62. For example, the wafers may be annealed, such as at a temperature of 900° C. to about 1100° C. for approximately one hour in an environment that includes nitrogen. Since the wafers do not include a barrier layer as described above, nitrogen diffuses into the wafers with a majority of the in-diffused nitrogen collecting at the gettering site 14. For each wafer, the nitrogen at the gettering site and, more typically, at and around the gettering site is then measured, such as by SIMS or the like. See block 64. Typically, the nitrogen is measured from the surface of the wafer to a depth within the wafer that is further removed from the surface of the wafer than the gettering site such that some portion of the wafer on both sides of the gettering site is analyzed.

Figure 6:
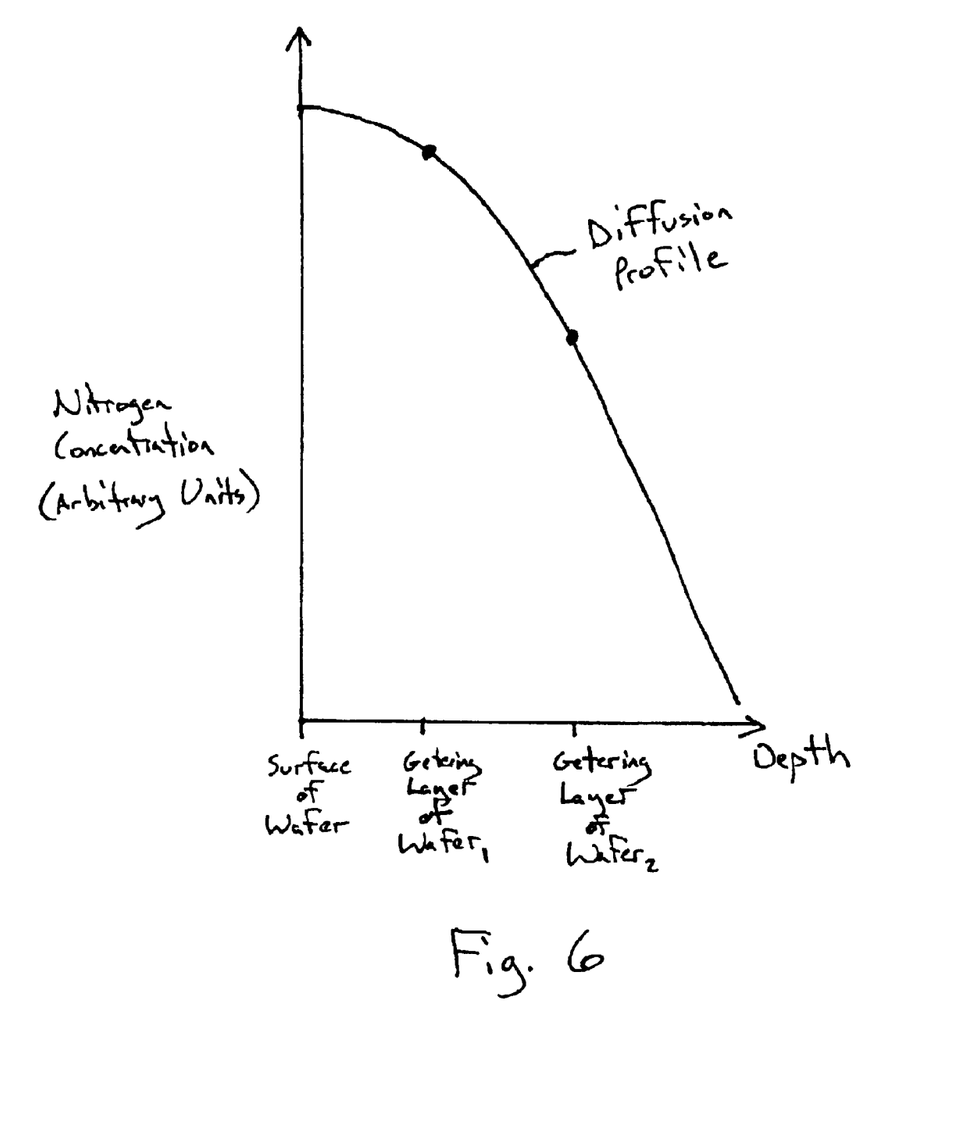
FIG. 6 is a graph representing a diffusion profile created according to one embodiment of the present invention.

Based at least partially upon the nitrogen measured at and around the gettering site 14 for each of the wafers 20, the diffusion coefficient D for nitrogen may be determined. See block 66. According to one embodiment, as illustrated in FIG. 6, the measured nitrogen concentrations are plotted against wafer depth for the two or more wafers. The nitrogen concentration at the wafer surface is constant, as nitrogen is sourced by the ambient. Using this plot, a diffusion profile for nitrogen in the wafers can be created, which profile will define a curve, such as a gaussian curve. In other words, the nitrogen concentration will gradually decrease with increasing wafer depth. Using computational techniques well known to those skilled in the art, such as nonlinear regression or Fourier analysis, the equation for the curve can be computed thereby providing the diffusion coefficient D for nitrogen through the wafers.

The diffusion coefficient D for nitrogen that is determined according to this aspect of the present invention may then be utilized to determine the concentration of nitrogen within a wafer 20 in the manner described above. However, the method of the present invention for determining the concentration of nitrogen within a wafer may, instead, utilize or rely upon a value for the diffusion coefficient D for nitrogen that is derived or provided in any other manner without departing from the spirit and scope of the present invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of determining a concentration of nitrogen within a wafer, the method comprising:
   providing a diffusion coefficient for nitrogen;
   gettering at least a portion of the nitrogen within the wafer to a gettering site;
   measuring the nitrogen at the gettering site; and
   determining the concentration of nitrogen within the wafer based upon the measurement of the nitrogen at the gettering site and the diffusion coefficient for nitrogen.

2. A method according to claim 1 further comprising depositing a barrier layer on the wafer prior to gettering at least a portion of the nitrogen within the wafer to the gettering site.

3. A method according to claim 1 wherein gettering at least a portion of the nitrogen within the wafer to the gettering site comprises heating the wafer.

4. A method according to claim 1 wherein the gettering site comprises a gettering layer, and wherein the method further comprises forming the gettering layer within the wafer prior to gettering at least a portion of the nitrogen within the wafer.

5. A method according to claim 4 wherein forming the gettering layer comprises implanting ions within the wafer to define the gettering layer.

6. A method according to claim 1 wherein measuring the nitrogen at the gettering site comprises measuring the nitrogen throughout a portion of the wafer including the gettering site.

7. A method according to claim 6 wherein determining the concentration of nitrogen within the wafer comprises dividing the nitrogen measured throughout the portion of the wafer that includes the gettering site by a diffusion length of nitrogen, which is dependent upon the diffusion coefficient for nitrogen.

8. A method of determining a concentration of nitrogen within a wafer, the method comprising:
   providing a wafer having a gettering site;
   heating the wafer;
   measuring the nitrogen at the gettering site following heating of the wafer; and
   determining the concentration of nitrogen within the wafer based upon the measurement of the nitrogen at the gettering site and a diffusion coefficient for nitrogen.

9. A method according to claim 8 further comprising depositing a barrier layer on the wafer prior to heating the wafer.

10. A method according to claim 8 wherein the gettering site comprises a gettering layer, and wherein the method further comprises forming the gettering layer within the wafer prior to heating the wafer.

11. A method according to claim 10 wherein forming the gettering layer comprises implanting ions within the wafer to define the gettering layer.

12. A method according to claim 8 wherein measuring the nitrogen at the gettering site comprises measuring the nitrogen throughout a portion of the wafer including the gettering site.

13. A method according to claim 12 wherein determining the concentration of nitrogen within the wafer comprises dividing the nitrogen measured throughout the portion of the wafer that includes the gettering site by a diffusion length of nitrogen, which is dependent upon the diffusion coefficient for nitrogen.

14. A method of determining a concentration of nitrogen within a wafer, the method comprising:
   providing a diffusion coefficient for nitrogen;
   forming a gettering site within the wafer;
   depositing a barrier layer on the wafer following formation of the gettering site;
   heating the wafer following the deposition of the barrier layer;
   measuring the nitrogen at the gettering site following heating of the wafer; and
   determining the concentration of nitrogen within the wafer based upon the measurement of the nitrogen at the gettering site and the diffusion coefficient for nitrogen.

15. A method according to claim 14 wherein forming the gettering site comprises forming a gettering layer within the wafer prior to depositing the barrier layer.

16. A method according to claim 15 wherein forming the gettering layer comprises implanting ions within the wafer to define the gettering layer.

17. A method according to claim 14 wherein measuring the nitrogen at the gettering site comprises measuring the nitrogen throughout a portion of the wafer including the gettering site.

18. A method according to claim 17 wherein determining the concentration of nitrogen within the wafer comprises dividing the nitrogen measured throughout the portion of the wafer that includes the gettering site by a diffusion length of nitrogen, which is dependent upon the diffusion coefficient for nitrogen.

19. A method for determining a diffusion coefficient for nitrogen comprising:

providing first and second wafers, each wafer having a gettering site and including an epitaxial layer, the epitaxial layer of the first wafer having a different thickness than the epitaxial layer of the second wafer;

permitting in-diffusion of nitrogen from the surrounding environment to the gettering site of each wafer;

measuring the nitrogen at the gettering site of each wafer following in-diffusion of nitrogen; and determining the diffusion coefficient for nitrogen based at least partially upon the nitrogen measured at the gettering site of each of the first and second wafers.

20. A method according to claim 19 wherein permitting in-diffusion of nitrogen comprises heating the wafers in a surrounding environment that includes nitrogen.

* * * * *